(12) United States Patent
Bradley

(10) Patent No.: US 11,350,581 B2
(45) Date of Patent: Jun. 7, 2022

(54) POLLINATING MACHINE

(71) Applicant: Terry G. Bradley, Howell, UT (US)

(72) Inventor: Terry G. Bradley, Howell, UT (US)

( * ) Notice: Subject to any disclaimer, the term of this patent is extended or adjusted under 35 U.S.C. 154(b) by 9 days.

(21) Appl. No.: 17/251,185

(22) PCT Filed: Jun. 12, 2019

(86) PCT No.: PCT/US2019/036820
§ 371 (c)(1),
(2) Date: Dec. 10, 2020

(87) PCT Pub. No.: WO2019/241419
PCT Pub. Date: Dec. 19, 2019

(65) Prior Publication Data
US 2021/0298253 A1      Sep. 30, 2021

Related U.S. Application Data

(60) Provisional application No. 62/683,764, filed on Jun. 12, 2018.

(51) Int. Cl.
*A01H 1/02*         (2006.01)

(52) U.S. Cl.
CPC .................. *A01H 1/027* (2021.01)

(58) Field of Classification Search
CPC ............ A01H 1/027; A01C 1/02; A01G 7/06
USPC ........................................ 47/1.41
See application file for complete search history.

(56) References Cited

U.S. PATENT DOCUMENTS

| | | | | |
|---|---|---|---|---|
| 1,866,219 A | * | 7/1932 | Nielsen | A01H 1/027 47/1.41 |
| 2,171,160 A | * | 8/1939 | Meiners | A01G 7/00 47/1.41 |
| 2,684,555 A | * | 7/1954 | Kantack | A01H 1/027 47/1.41 |
| 2,685,149 A | * | 8/1954 | Hvistendahl | A01H 1/027 47/1.41 |
| 4,087,937 A | * | 5/1978 | Meader | A01H 1/027 47/1.41 |
| 4,383,389 A | * | 5/1983 | Bezzerides | A01H 1/027 47/1.41 |
| 2021/0045306 A1 | * | 2/2021 | Baldet | A01B 59/064 |
| 2021/0298253 A1 | * | 9/2021 | Bradley | A01H 1/027 |

* cited by examiner

*Primary Examiner* — Christopher D Hutchens
(74) *Attorney, Agent, or Firm* — Dobbin IP Law, P.C.; Geoffrey E. Dobbin

(57) ABSTRACT

A pollination machine (10) with improved cross-pollination abilities may feature a plurality of pollen recirculation chambers with an air circulation manifold (130A, 131A, 133A, etc.) connecting them in a manner that air in one chamber (30A), together with associated pollen, is removed from the one chamber and redirected to a second (30B), and so on until air is returned to the first (30A). The chambers' initial roller entrances (118) will serve to trip blossoms and release both pistol and pollen but a current in the air circulation manifold contains and will deposit foreign pollen grains on the plants' stigmas before they are inundated by the blossoms' own pollen. The air current also collects the plants' pollen and carries it to other chambers so that other plants will be cross-pollinated.

8 Claims, 14 Drawing Sheets

POLLINATING MACHINE

CROSS-REFERENCES TO RELATED APPLICATIONS

This Application claims priority as a non-provisional perfection of prior filed U.S. Application No. 62/683,764, filed Jun. 12, 2018, and incorporates the same by reference in its entirety.

FIELD OF THE INVENTION

The present invention relates to the field of agriculture and more particularly relates to a machine which will effectively cross-pollinate certain agricultural crops.

BACKGROUND OF THE INVENTION

The world's primary forage crop for beef cattle, dairy cows, horses, etc., is alfalfa (*Medicago sativa*). Being in great demand, alfalfa seed is, nonetheless, very expensive and financially risky to produce. Throughout time, the production of alfalfa seed has been consistently successful only by applying pollinators, specifically Alfalfa Leafcutter Bees (*Megachile rotundata*), in extremely large numbers. Applying such pollinators is a very costly endeavor and is fraught with numerous challenges. Unlike honeybees, which are not very effective as alfalfa pollinators, Alfalfa Leafcutter Bees do not "winter-over" in colonies, and have short, single-season lives. Therefore, farmers must take great care in handling the bees, including having to artificially incubate and chill the bee prepupae to synchronize their emerging (hatching) precisely with the blooming of the alfalfa field. In addition, dealing with parasites, predators, diseases, and pesticides, which often destroy large percentages of the entire bee crop, are common. To add to the financial risks, the alfalfa-seed field must be sprayed against crop-destroying pests multiple times each season with precise timing. These pests include: Lygus Beetles, Aphids, Armyworms, Grasshoppers, etc., which can otherwise cause complete crop failure. Unfortunately, these sprays also can kill the bees (which at this point, are working in the field) unless extremely expensive pesticides, designed to selectively kill the pests while hopefully sparing the costly, crucial bees, are used. Even if all these challenges can be overcome, cool, cloudy, or breezy weather can "ground" the Leafcutter Bees during the "bloom-window", causing a failed seed crop. Perhaps worst of all, many scientists predict the eventual demise of pollinating bee-species, seriously threatening the future success of all pollination, including alfalfa seed production.

For these reasons, over the past decades, countless botanists, entomologists, alfalfa seed producers, etc., have spent vast amounts of time and resources, trying to devise "artificial" or "mechanical" means of pollinating alfalfa blossoms on a large scale, but to no avail.

A careful study of the alfalfa blossom reveals that within each flower are two Keel Pedals, fused together, housing a Pistol. The pistol develops as a curved, bow-shaped shaft, but is held in a straight form by the keel pedals encasing it; hence the pistol, in this condition, is spring-loaded. Atop this pistol is located the Stigma, which is surrounded by 10 Stamens. Atop each stamen is an Anther. Each anther contains the crucial pollen. Each alfalfa plant is self-sterile; no pollen from a plant will pollinate any blossom from anywhere on the same plant. Foreign pollen grains must "Cross-Pollinate" by attaching to the stigma of a blossom on a different plant and then germinate into "Pollen Tubes" which travel down through the pistol and fertilize the Ovules, thus beginning the seed development.

When a Leafcutter Bee lights upon the alfalfa flower, it claws into the fused keel pedal enclosure to get the pollen. As the enclosure begins to tear open, the "spring-loaded" pistol breaks free, and instantaneously snaps down on the hairy head of the bee, which is covered with foreign pollen from other alfalfa plants it has visited. This action deposits a few grains of foreign pollen directly onto the stigma (atop the pistol), successfully pollinating that flower, which can then produce several alfalfa seeds, becoming a spiral-shaped Seed Pod. This "Tripping" of the blossom is mandatory to expose the stigma to foreign pollen. If the blossom is not tripped, no pollination occurs.

Those skilled in the art throughout time have observed this tripping process and have artificially tripped the blossoms by squeezing them between their fingers, erroneously assuming a machine could do this on a massive scale, they could then produce large amounts of alfalfa seed. In reality, when each flowers' pistol "trips" without a foreign-pollen-covered bee underneath it, the stigma, atop the pistol, and pollen-laden anthers surrounding it, strike the adjacent Standard Pedal and shakes only its own self-sterile pollen onto its own stigma, completely covering the stigma with its own ineffective pollen burst. This also inhibits any foreign pollen grains from having room to adhere to the stigma, even in the unlikely event that foreign pollen grains were to later encounter the now-clogged stigma. Its own pollen being self-sterile, the flower remains un-pollinated and produces no seed.

Prior mechanical pollinators have been developed, but many of them fail to adequately trip the blossoms. These devices also fail in that they do not cross-pollinate. In fact, in the process of tripping the blossom, prior devices also initiate the pollen burst and clog the stigma with self-sterile pollen. To date, no man-made apparatus has ever been designed which could successfully simulate the intricate pollination procedure of bees on a large scale. This intricate sequence, perfected only by nature, is crucial to the development of alfalfa seed. What is needed then, is a machine which will trip the blossoms and deposit enough foreign pollen grains on the stigma before the blossom's own pollen inundates its own stigma, thus providing pollen from other plants to cross-pollenate each blossom.

The present invention represents a departure from the prior art in that the pollinator of the present invention allows for tripping each blossom, while depositing pollen from various individual plants under or on the tripping stigma before the stigma is covered with only its own self-sterile pollen. In addition, it accomplishes the removal of each blossom's pollen to be deposited on other plants.

SUMMARY OF THE INVENTION

In view of the foregoing disadvantages inherent in the known types of pollinators, an improved cross-pollination machine may provide a plurality of pollination stations with enclosed chambers that meets the following objectives: that it successfully trips each blossom, that it removes pollen from each blossom, and that it circulates pollen from other blossoms in the chamber environment to achieve cross-pollination. As such, a new and improved pollinator may comprise two sets of mostly sealing rollers to isolate each chamber and a vacuum and blow-back system in order to accomplish these objectives.

The more important features of the invention have thus been outlined in order that the more detailed description that follows may be better understood and in order that the present contribution to the art may better be appreciated. Additional features of the invention will be described hereinafter and will form the subject matter of the claims that follow.

Many objects of this invention will appear from the following description and appended claims, reference being made to the accompanying drawings forming a part of this specification wherein like reference characters designate corresponding parts in the several views.

Before explaining at least one embodiment of the invention in detail, it is to be understood that the invention is not limited in its application to the details of construction and the arrangements of the components set forth in the following description or illustrated in the drawings. The invention is capable of other embodiments and of being practiced and carried out in various ways. Also, it is to be understood that the phraseology and terminology employed herein are for description and should not be regarded as limiting.

As such, those skilled in the art will appreciate that the conception, upon which this disclosure is based, may readily be utilized as a basis for the designing of other structures, methods, and systems for carrying out the several purposes of the present invention. It is important, therefore, that the claims be regarded as including such equivalent constructions insofar as they do not depart from the spirit and scope of the present invention.

DETAILED DESCRIPTION OF THE PREFERRED EMBODIMENT

With reference now to the drawings, a preferred embodiment of the pollinating machine is herein described. It should be noted that the articles "a", "an", and "the", as used in this specification, include plural referents unless the content clearly dictates otherwise.

Figure 1:
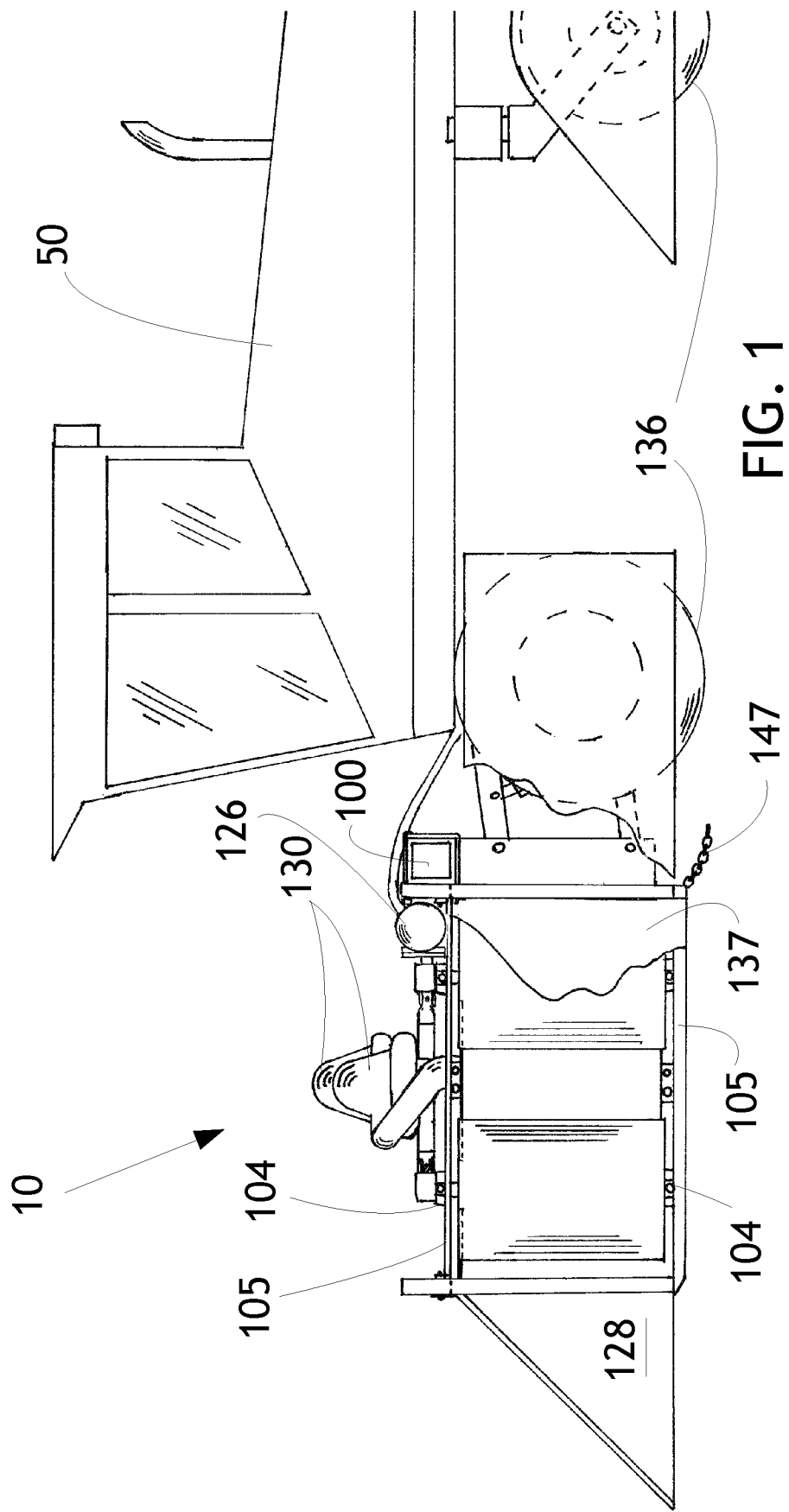
FIG. 1 is a side elevation of a pollinating machine being carried by a swather tractor.
Figure 2:
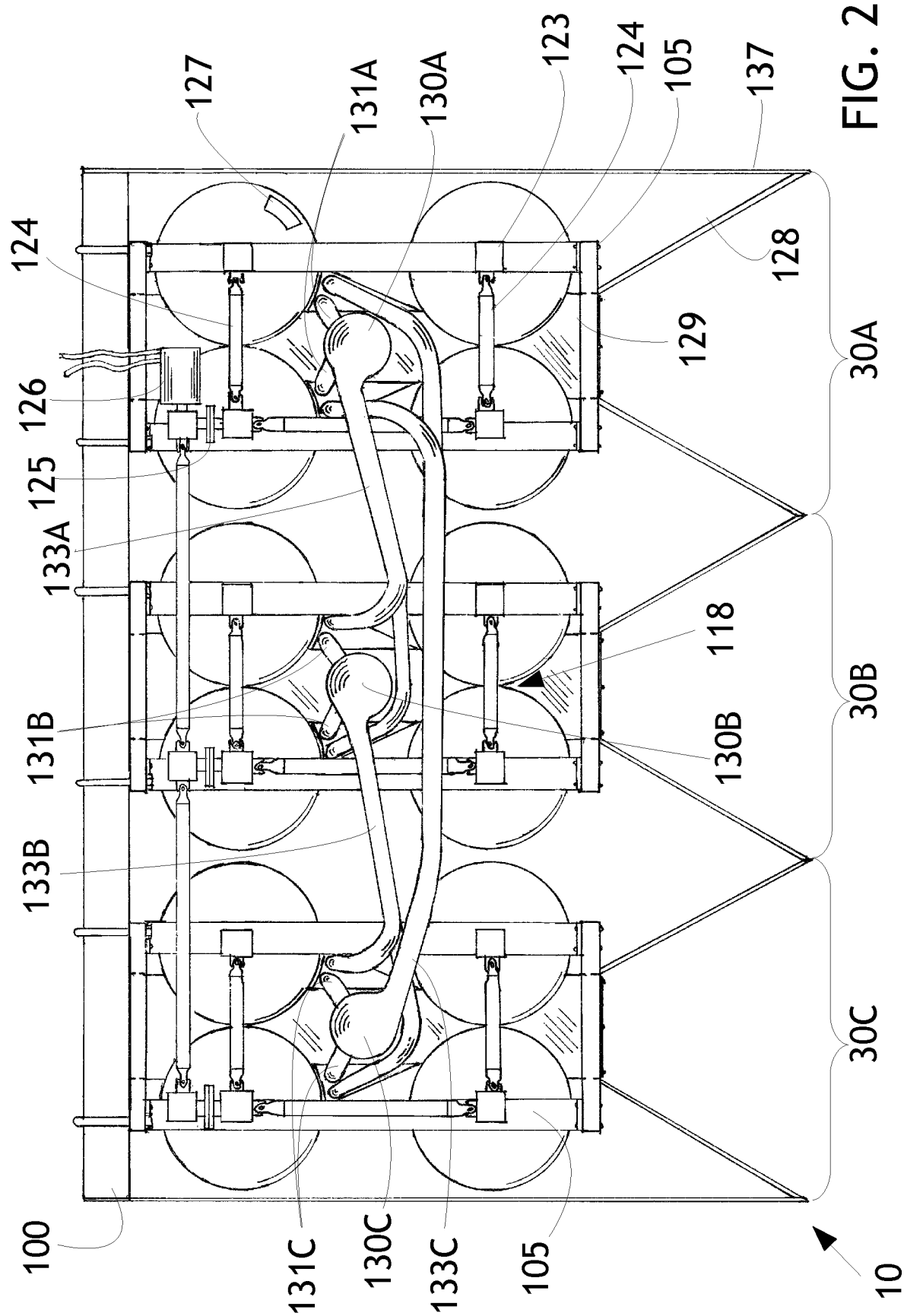
FIG. 2 is a top plan view of the pollinating machine of FIG. 1.
Figure 3:
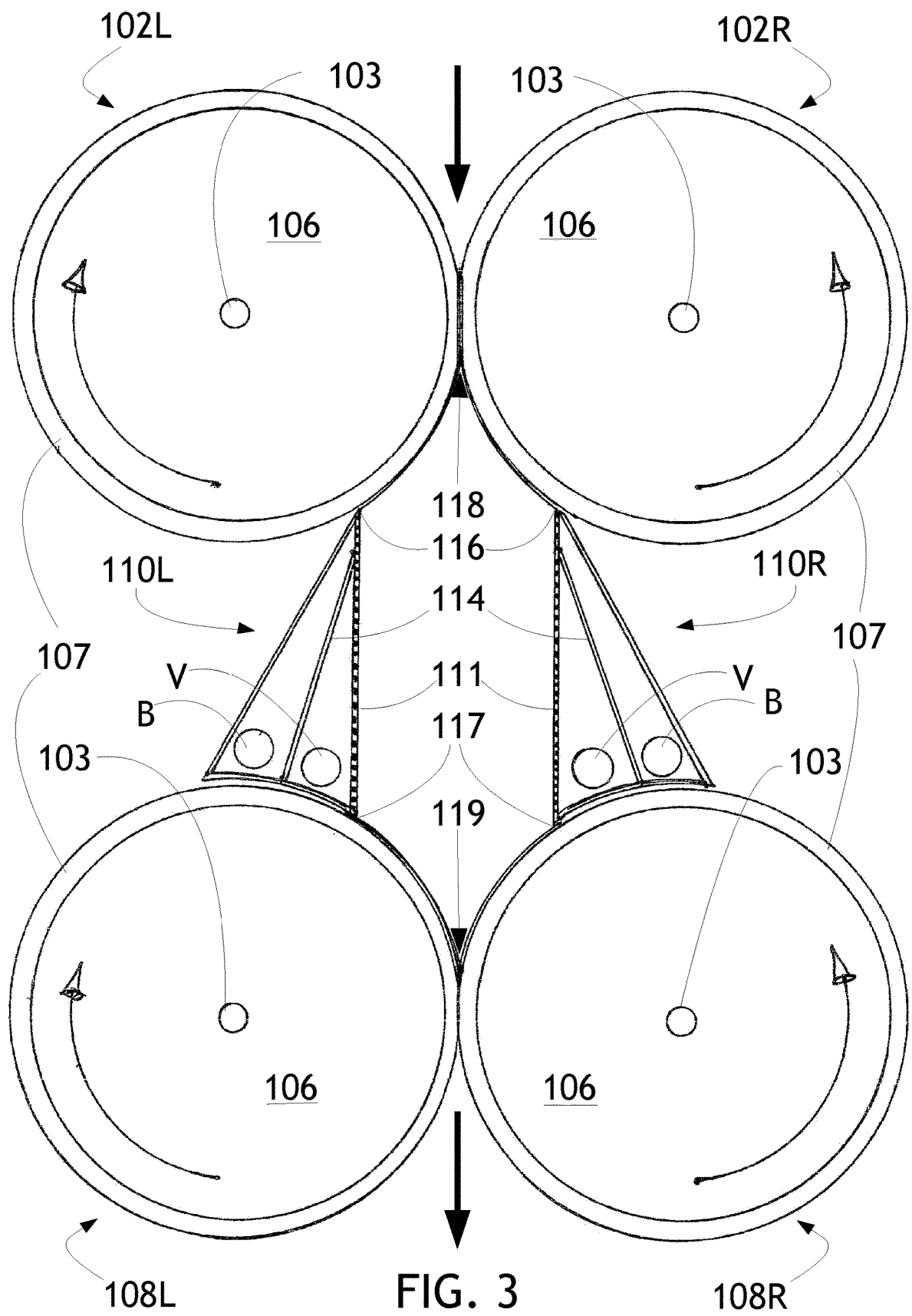
FIG. 3 is a top plan view of a single pollen recirculation chamber used in the pollination machine of FIG. 1, uncovered.
Figure 4:
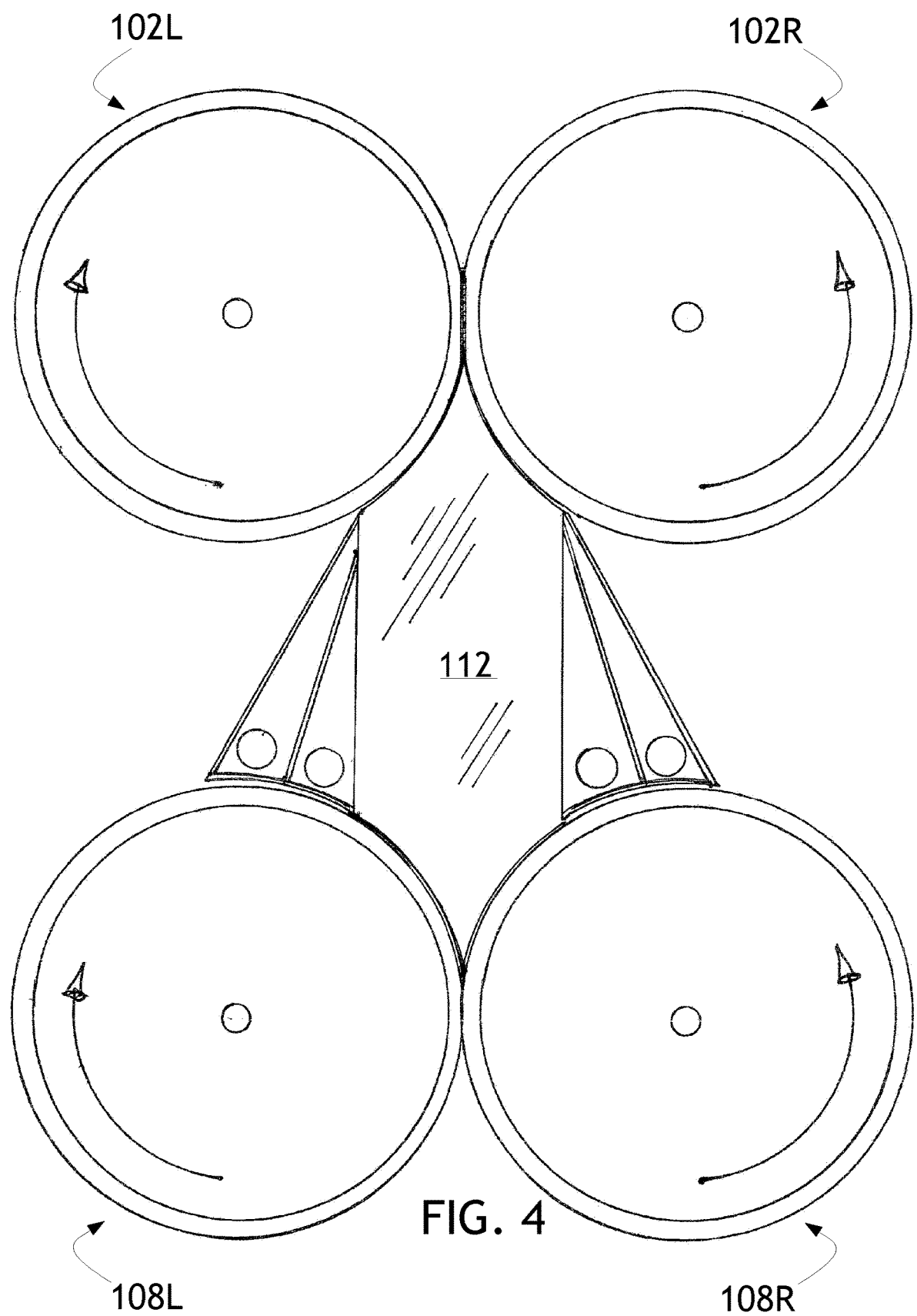
FIG. 4 is a top plan view of a single pollen recirculation chamber used in the pollination machine of FIG. 1, covered.
Figure 5:
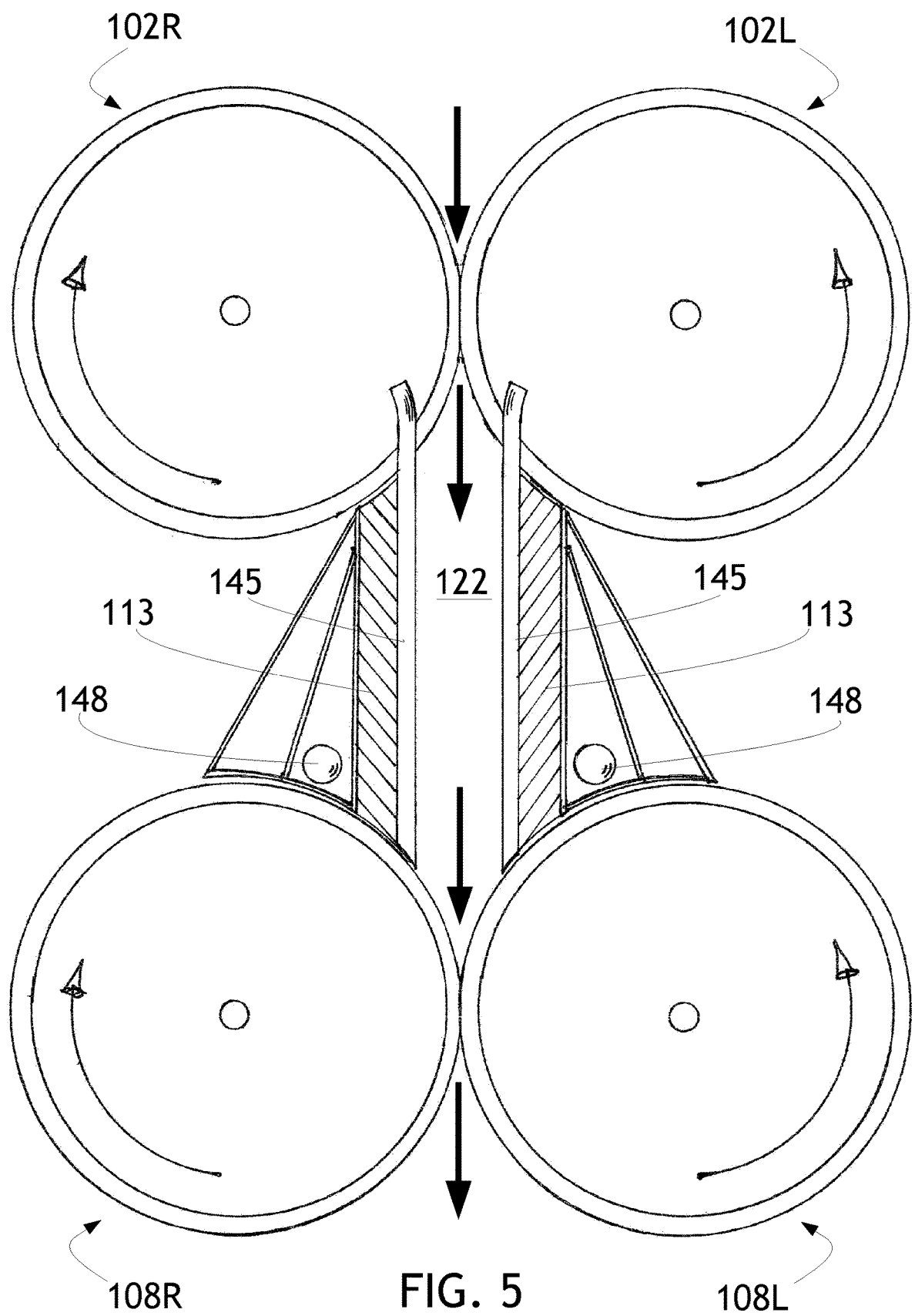
FIG. 5 is a bottom plan view of a single pollen recirculation chamber used in the pollination machine of FIG. 1.

As shown in FIG. 1, a pollinating machine (10), intended for use with plants such as, but not limited to, alfalfa, which can be mounted to (or pulled behind) a vehicle, such as a common, self-propelled swather-tractor (50), for example, in place of the standard swather-header. The pollinating machine is raised or lowered (by hydraulic, or other means) in relation to the ground, depending upon the height of the plants to be treated. Preferably, the pollination machine (10) consists of at least one, if not two or more identical "pollinating stations" (130), as shown in FIGS. 2 and 3, mounted adjustably to a rigid toolbar (100), which is mounted to the tractor (34). Each pollinating station (130) interacts with another pollinating station (which is pollinating a separate row of plants) to facilitate full cross-pollination of every blossom treated, as will be described. The herein-described embodiment consists of three pollinating stations. Each pollinating station consists of two front vertical companion-rollers (see FIG. 3) (labeled "102L" for left, and "102R" for right), mounted on vertical axels (103), which are mounted in adjustable bearing-blocks at the opposite ends of said axels (see FIG. 1) (104), which are mounted to a rigid frame (105). The pair (top and bottom) of adjustable bearing blocks (104) of each roller are adjustable so as to draw nearer too, or farther away from its companion roller, with precision adjustment, lockable in place. Each roller is made of round, rigid material, such as, but not limited to, metal or plastic pipe, affixed to its centralized shaft with horizontal discs or spokes (106), as shown in FIG. 3. Surrounding each roller is a replaceable band (or tube) of sheet metal (or other material), which is clamped firmly around the rigid roller. Affixed to this band (or tube) is a layer of soft material (107), which, in place, completely covers the roller's radial surface with a uniform layer of soft, durable material, such as, but not limited to, thick Neoprene 10-A Shore rubber, or a "multi-hardness" material having a thin, stronger surface, and a thick, softer, compressible underlayer, which allows bulkier foliage to pass between said rollers. This thick, compressible material "self-adjusts" to bulkier or less bulky foliage passing between the later-described rollers, while maintaining a relatively constant pressure on the foliage passing between said rollers. Smooth, adjustable-pressure pneumatic rollers or tires, which would absorb bulkier foliage passing between the pair would also be within the scope of the described invention. The two front companion-rollers (102L & 102R) are adjusted so as to be compressed firmly toward each other; the purpose of which is to roll the plants between said rollers, pressing upon each blossom sufficiently as to "collapse", and therefore, "trip" each spring-loaded pistol therein contained, as each blossom emerges from the pressing front companion-rollers (102L & 102R). Positioned behind, and, pertaining to the straight travel of the machine, directly in line with the front companion-rollers, are two rear companion-rollers (labeled "108L" for left and "108R" for right), also mounted in adjustable bearing blocks (104) which are mounted to the rigid frame (109), identical to the afore described front rollers. However, the two rear companion-rollers (108L), (108R) are mounted and fixed to only make contact with each other, having very light compression toward each other. (The purpose of these rear companion-rollers is mainly to restrict air from passing between them, as will be explained later). In-between the front left roller (102L) and the rear left roller (108L), and oppositely, in-between the front right roller (102R) and the rear right roller (108R), is a left and a right, rigid, hollow, three-sided structure (labeled "110L" for the left three-sided structure, and "110R" for the right three-sided structure) running up and down the full vertical height of the rollers, as hereto described: The face of each structure consists of a perforated (metal, plastic, etc.) plate (111), (with approximately ⅛-inch holes or slots in close proximity to each other). The other two walls of the three-sided structure, shown in FIGS. 4 and 5, are of thin but rigid, solid plate, as is the top plate (112) and the bottom (separated) plate (113). Inside the afore described three-sided structure, is a baffle (114), or solid plate, running vertically, from top to bottom, separating the whole three-sided structure into two separate air-duct passageways, one labeled "15B" (for blow) and the other labeled "115V" (for vacuum). In the top-plate are two holes, one accessing the inside of air-duct passageway (115B), labeled (B) and one accessing the inside of air-duct passageway (115V), labeled (V), allowing forced (or vacuumed) air to pass through them. In the bottom plate of air-duct passageway (115V), is a clean-out hole with a removable cap (FIG. 5) (148). The afore described entire bottom plate can be removable for cleaning purposes. It will be noted that air-duct passageway (105V) consists of three sides: The first side consists wholly of the perforated plate (111), the second side consists of the inner baffle-plate (114), and the third side consists of a solid plate.

Figure 13:
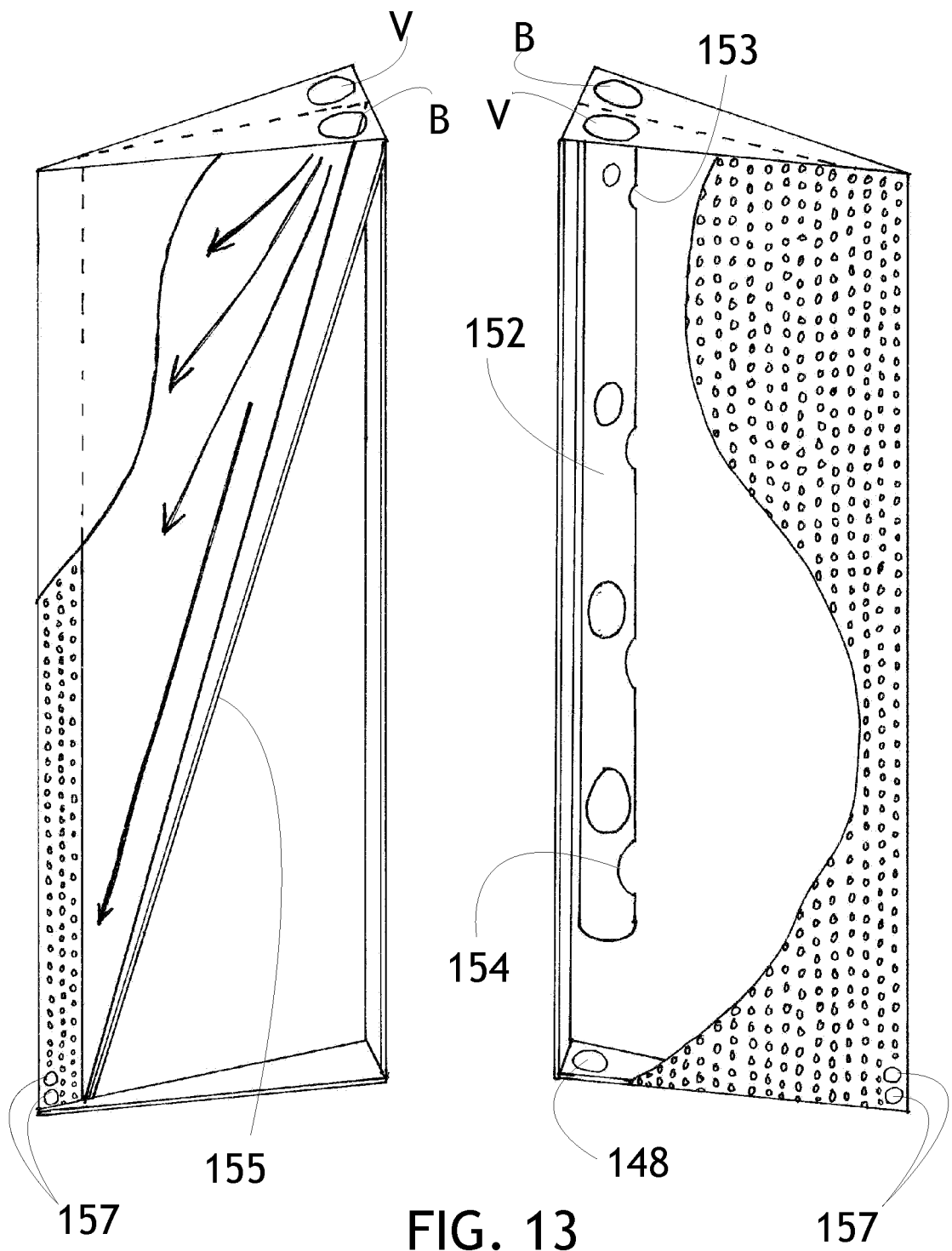
FIG. 13 is a partial sectional view of two vacuum and blower structures detailing internal structure.
Figure 14:
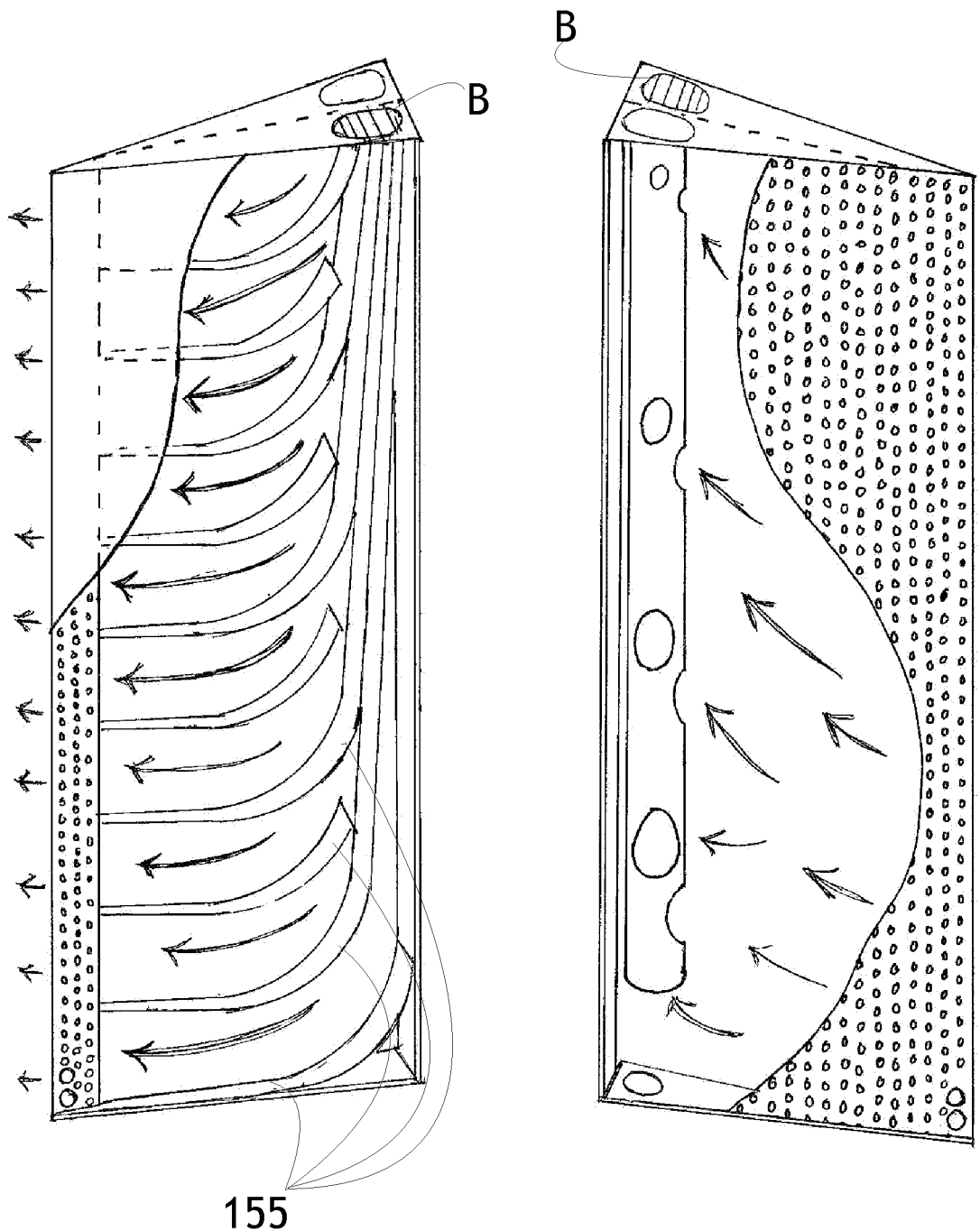
FIG. 14 is a partial sectional view of two alternate vacuum and blower structures detailing internal structure.

It is also noted, in FIG. 13, that extending down through the top-plate hole of air-duct passageway (115V), is an air-intake-pipe (152) with small holes (153) at the top, and increasingly larger holes (154) running down the length of said pipe, to the open bottom. This embodiment ensures that air is drawn, or vacuumed in, evenly throughout the entire perforated face plate (111). Air duct Passageway (115B) (or the "blower vent") consists of 3 sides, but differs as follows: approx. 90% (the rear portion) of the first side is made of the solid baffle-plate (14), and approximately 10% (the front portion) is made of the perforated plate (111), the second side consists of a solid plate, and the third side consists of a solid plate. Inside this same structure is at least one "air-directing" fin (155), which directs the in-coming flow of pollen-laden air towards, and evenly, out through the front 10% of the afore-mentioned perforated plate. It is noted that at the bottom of the afore-mentioned 10% perforated plate, are several larger holes which act as "clean-out" ports (157) to discard any material which might otherwise accumulate in the bottom of said air-duct passageway (115B). It is also here noted, that other types of air-directing designs, such as perforated vacuum rollers, perforated conveyor-belts, etc. may be utilized, all of which are within the scope of the subject invention. One variation of this structure is shown in FIG. 14, where a plurality of air-directing fins 155 is used to divide the column of air in the air duct passageway (and associated pollen) into smaller sections for a more directed distribution of pollen.

Figure 6:
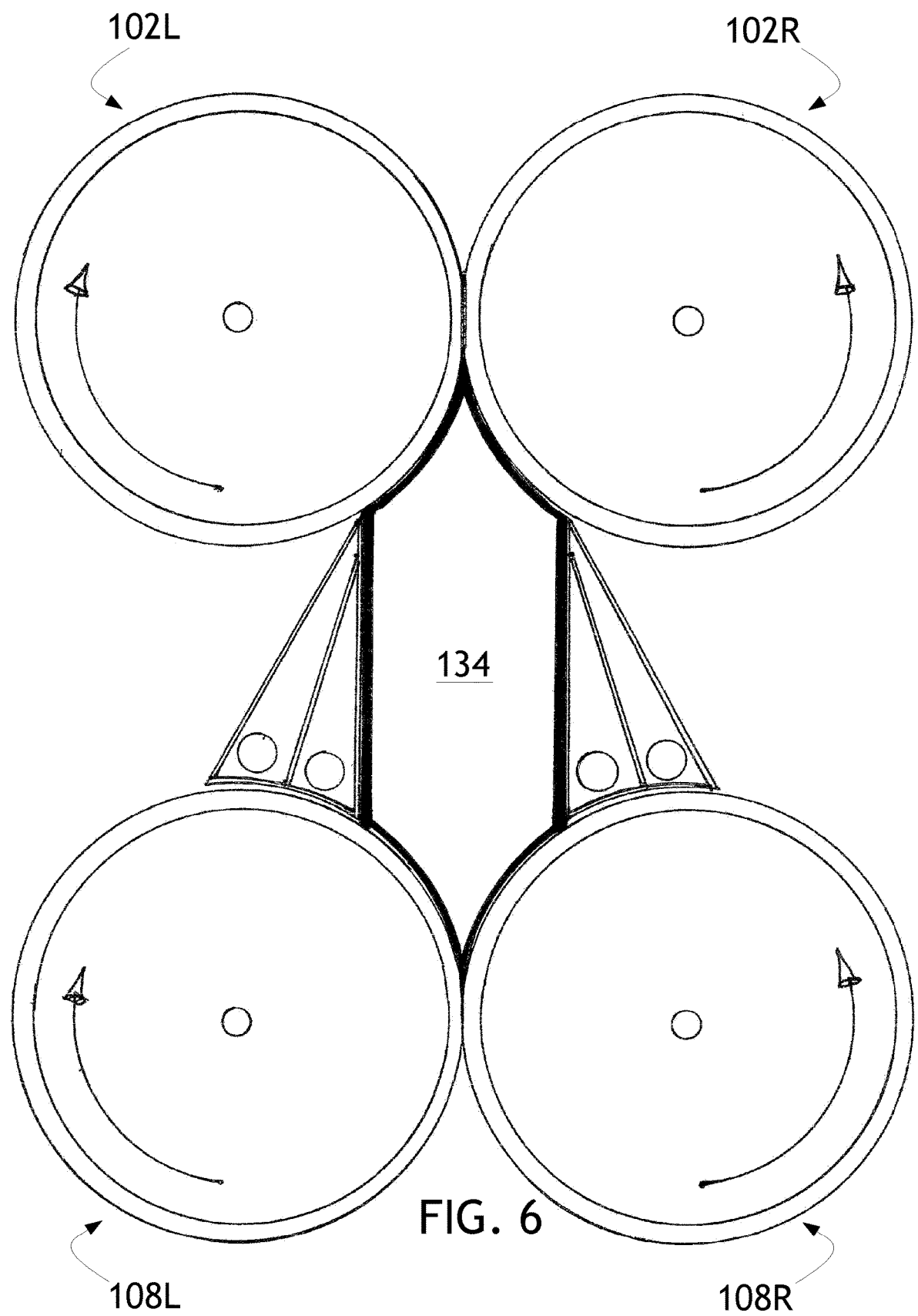
FIG. 6 is a top plan view of a single pollen recirculation chamber used in the pollination machine of FIG. 1, highlighting the chamber.

The three-sided structures afore described, face each other (see FIG. 3). That is to say, the right three-sided structure (110R) (positioned between the right-front roller and the right rear roller), and the left three-sided structure (110L) (positioned between the left-front roller and the left-rear roller), face each other (that is, their perforated plates face each other), with several inches of space between them. The leading-edge of the right three-sided structure (110R) is positioned with a very small gap between it and the right front roller (116), and the trailing edge is positioned with a very small gap between it and the right-rear roller (117), so as to virtually seal-off any air from passing through the gap. The afore described positioning of the right three-sided structure (110R) also applies, oppositely, to the positioning of the left three-sided structure (110L), in relation to the left-front and left-rear rollers. The two opposing, perforated faces of the three-sided structures are spaced sufficiently apart from each other to allow full alfalfa plants, emerging from the front rollers (102L, and 102R), to slide loosely between them. The inner space between the perforated "face-plates" (111), from the connecting seam (118) of the front two rollers, to the connecting seam (119) of the rear two rollers, constitutes a virtually enclosed "pollen-recirculating-chamber" (see bold outline, FIG. 6) (134). The purpose of these rear companion-rollers (118L & 118R) is mainly to restrict air-borne pollen from passing between them; in other words, said rear companion-rollers complete the full enclosure of said pollen recirculating chamber. With a plate sealing the top of said chamber (112) (FIG. 4), and two separated plates sealing the bottom of said chamber (113) (FIG. 5), entailing a slotted opening (lined with smooth, round rods to facilitate the stems sliding along them) (145) which spans the length of the chamber, allowing the thin plant-stems to travel, unrestricted, along the bottom of the chamber (122), this afore-described configuration, as earlier stated, creates a virtually sealed pollen recirculating chamber.

Figure 8:
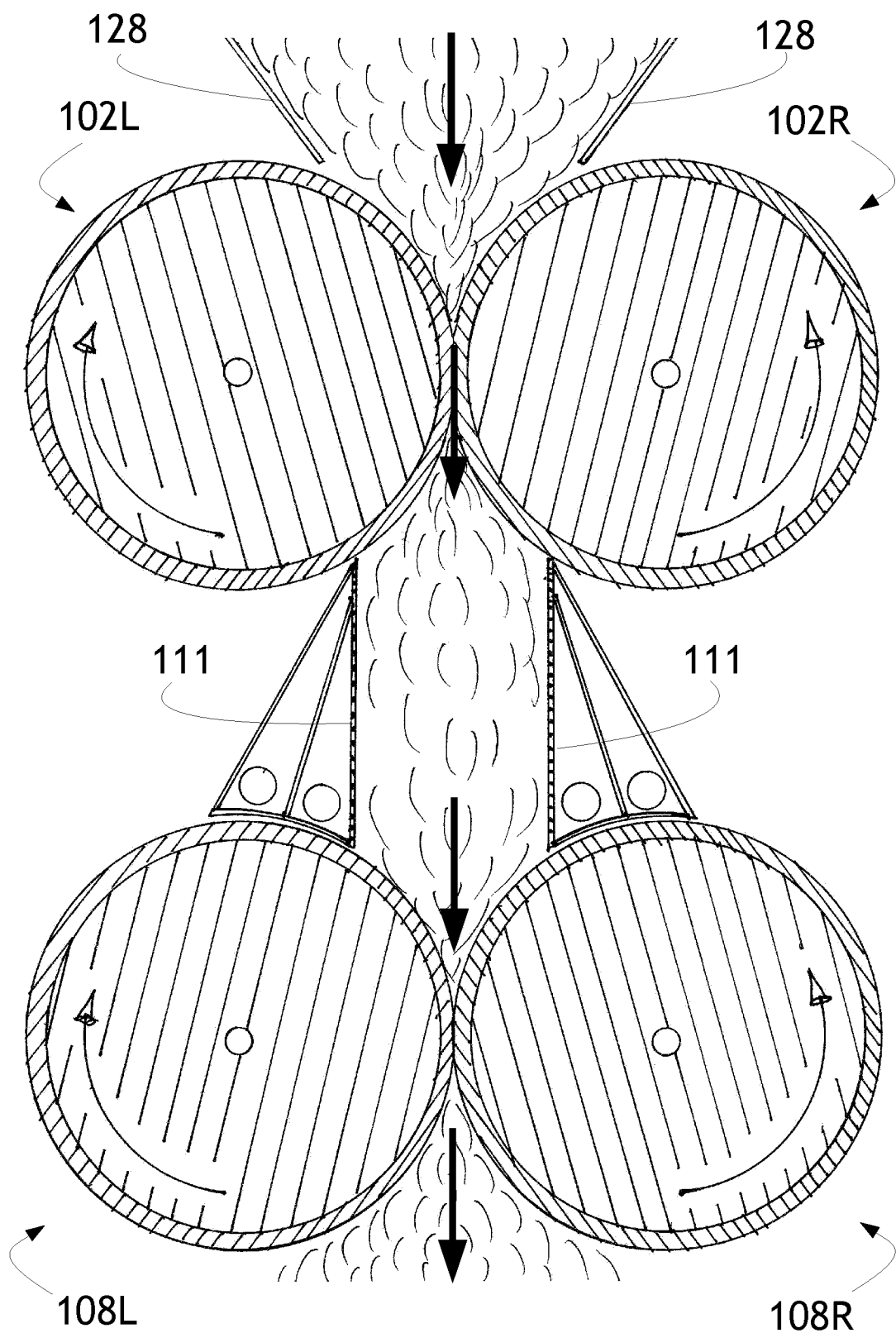
FIG. 8 is a top plan view of a single pollen recirculation chamber used in the pollination machine of FIG. 1, in use.
Figure 9:
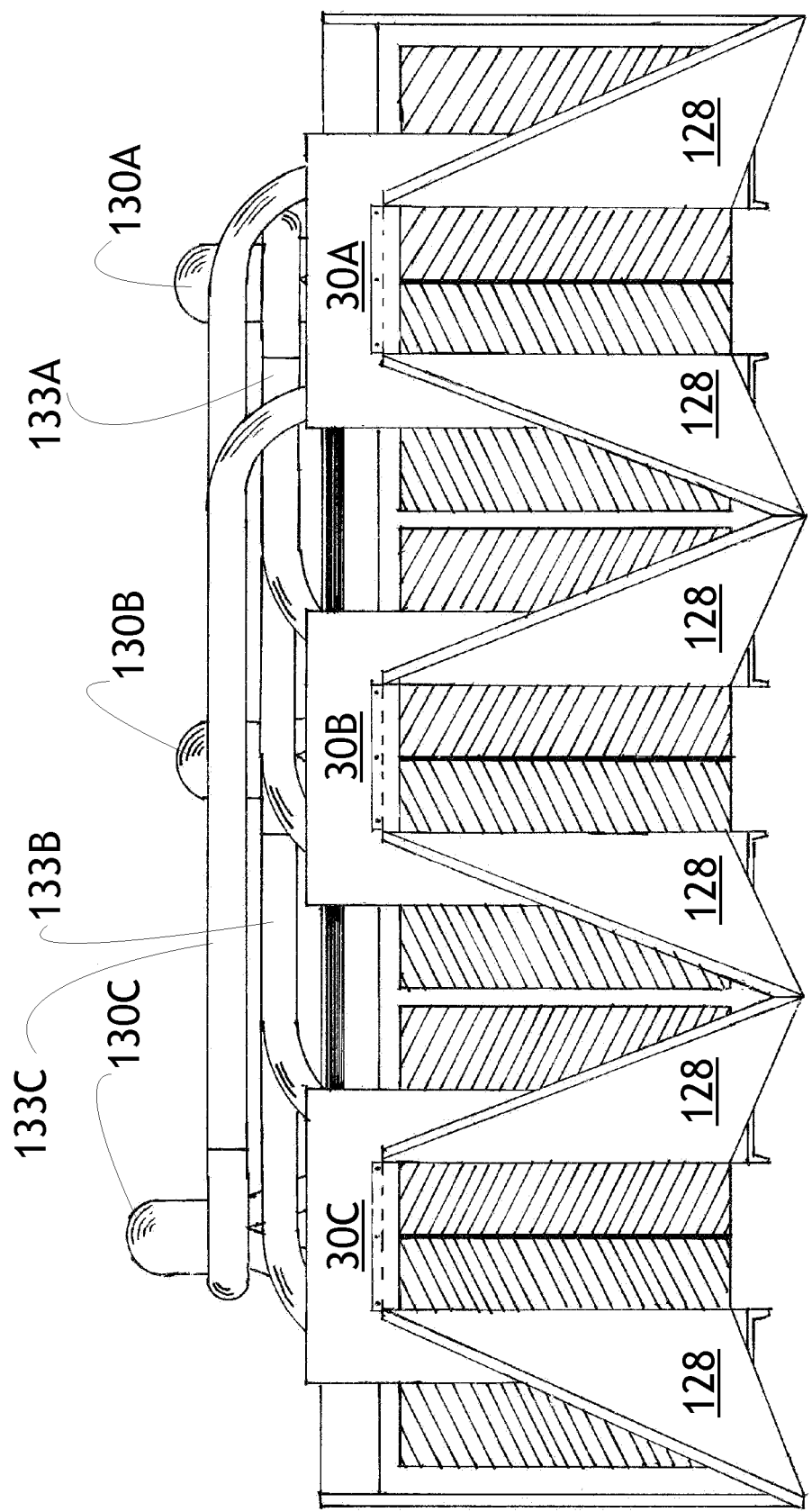
FIG. 9 is a front elevation of a pollinating machine of FIG. 1.
Figure 10:
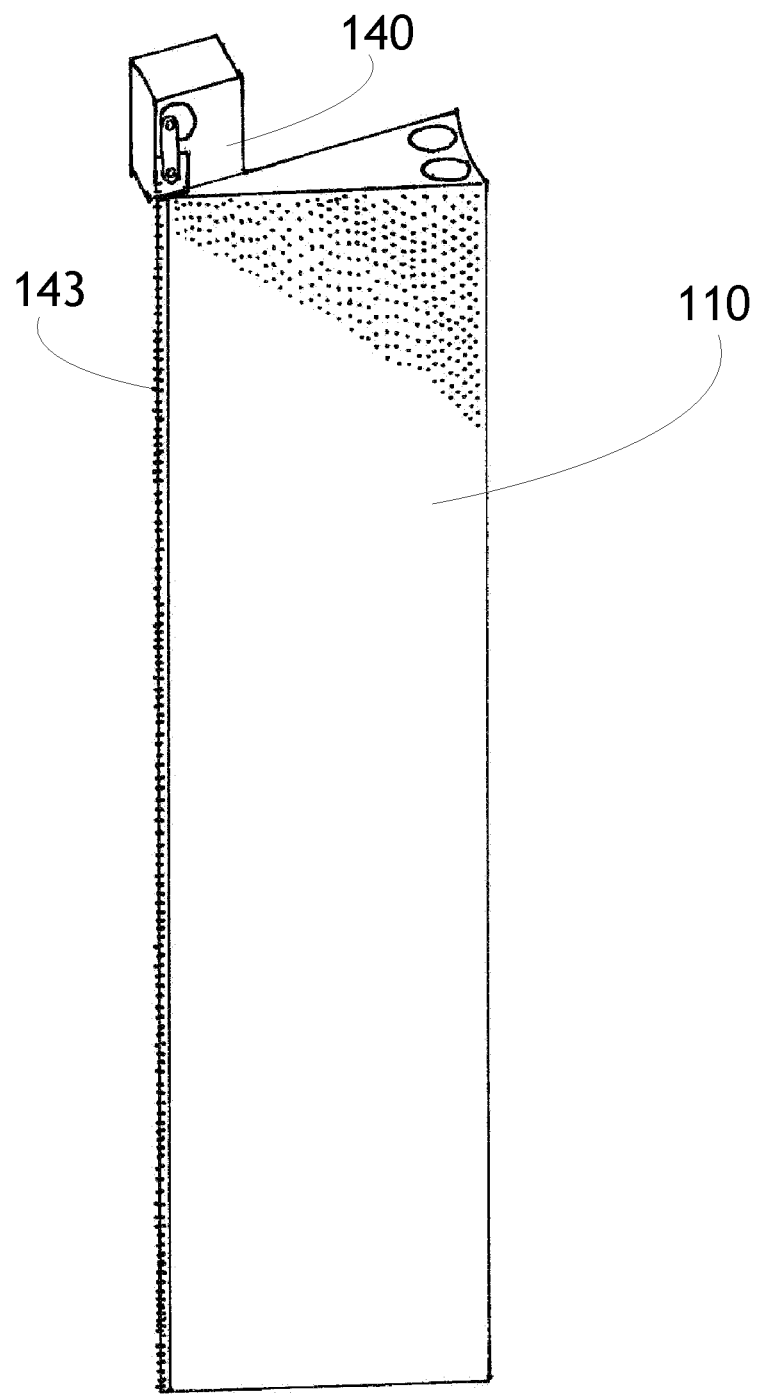
FIG. 10 is a perspective view of a vacuum and blower structure with an anti-clogging knife.
Figure 11:
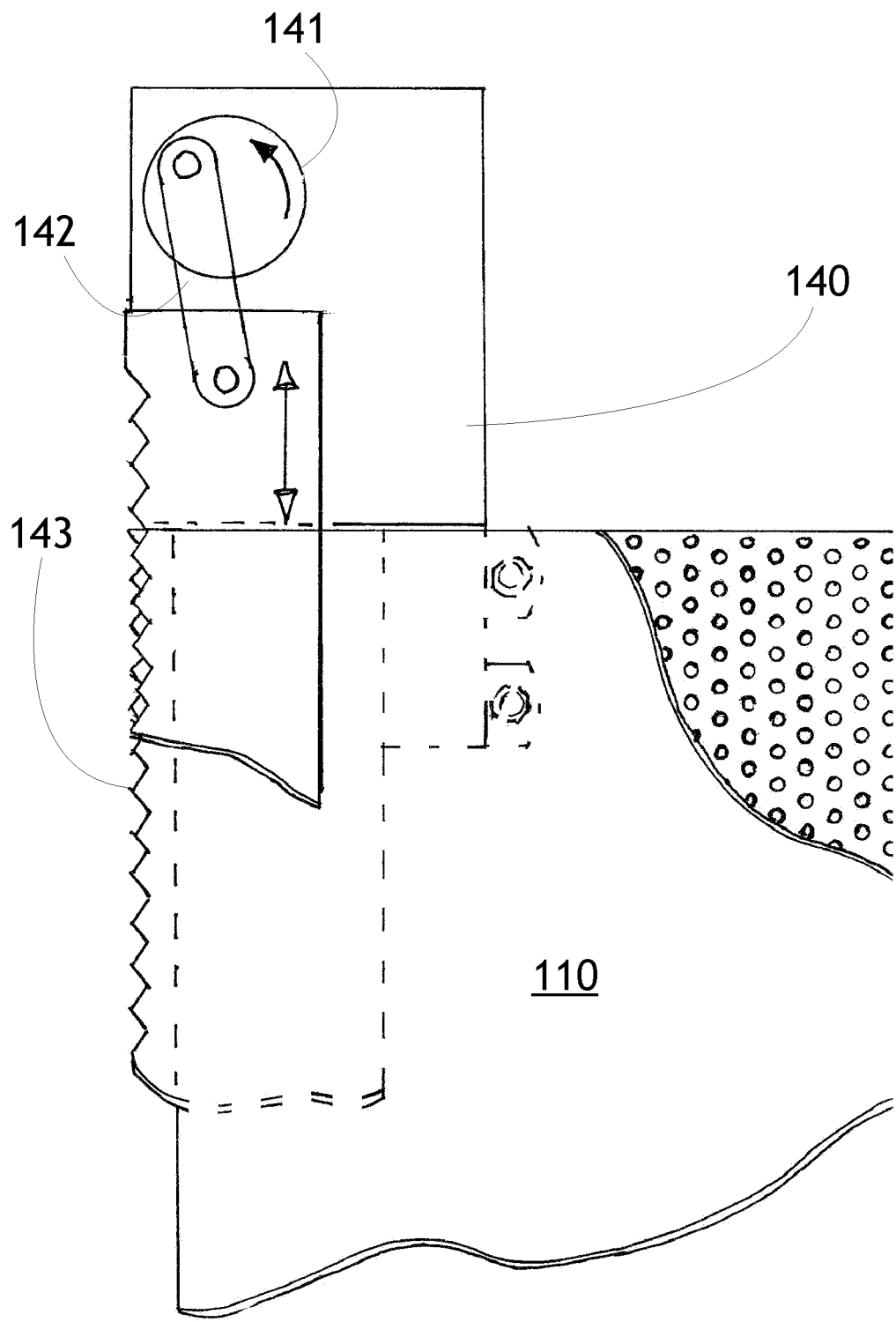
FIG. 11 is a close-up, side elevation of the vacuum and blower structure and knife of FIG. 10.
Figure 12:
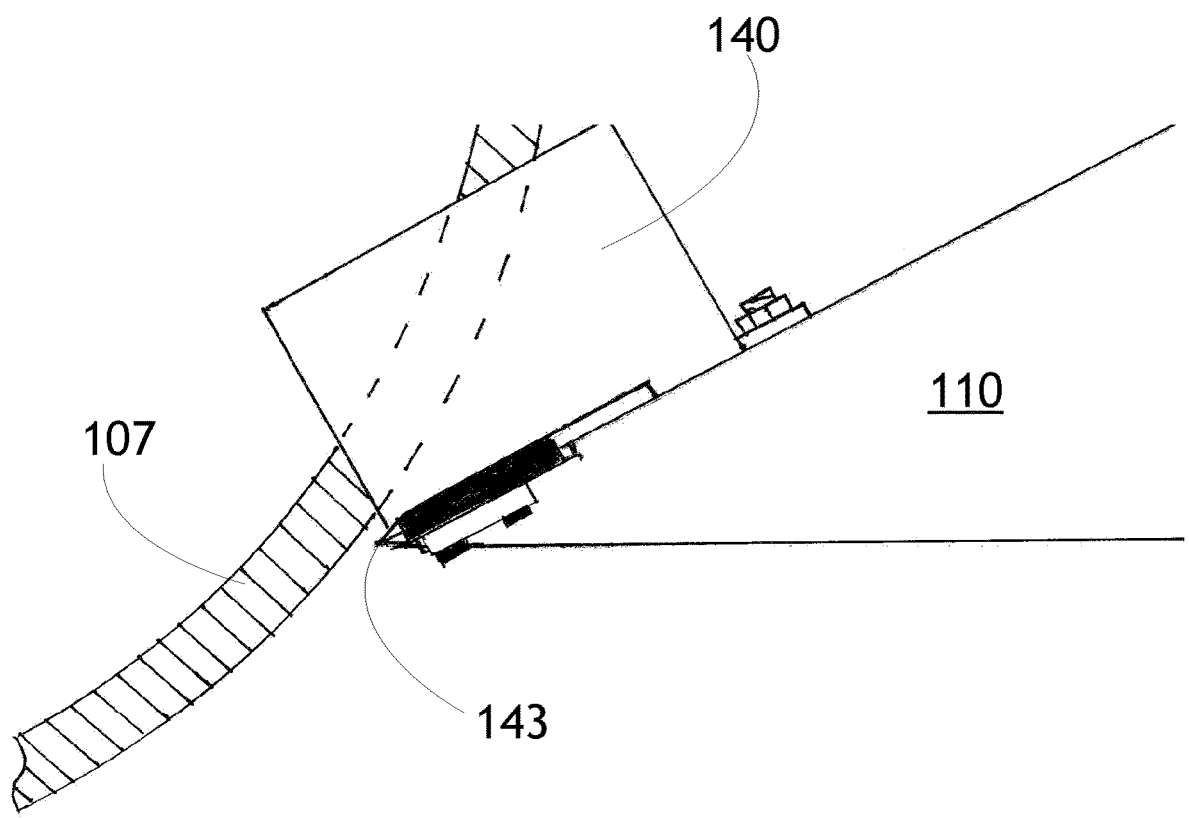
FIG. 12 is a top plan view of the vacuum structure and anti-clogging knife of FIG. 11.

The top of each roller-axel (103) is connected to a series of gear-boxes (123), drive-shafts (124), and slip-clutches (125) (FIG. 2), all ultimately powered by an adjustable-speed hydraulic motor (126), or other source of power, and mounted to the rigid frame (105). (Alternatively, a series of roller-chains and sprockets can be used, or any other means of turning the drum-axels in unison). Said driveshafts and gearboxes are configured so as to rotate each pair of rollers in an opposing direction in relation to each other (see FIG. 8), so as to propel the plants into and through the front companion-rollers (102L & 102R) (as the machine travels forward), past the perforated, three-sided-structure face-plates (111), and into and through the rear companion-rollers (108L & 108R), the plants thus exiting the "pollen recirculating chamber". Thus, in operation, the entire machine drives through the plants at precisely the same speed that the rollers are feeding the plants through them (the synchronized speed of the rollers, in relation to the ground-speed of the tractor, being controlled by micro-processors) (127), shown in FIG. 2. In addition, each pollinating station is equipped with fixed left and right "funneling" wings, or guides (128) (FIG. 9), which continuously lift and guide the plant-foliage into the front companion-rollers (102L & 102R). There are also guards which direct foliage away from the tires (136), and guards (137) which direct foliage away from the opposing motion of the outside of the rollers. In addition, the leading-edge of both the left three-sided structure (110L) and the right three-sided structure (110R) can consist of a vibrating, ultra-sonic, or reciprocating, (etc.) knife (FIGS. 10-12) (143), powered by a vibrator or linked (142) to a reciprocating motor (140) with a rolling drive (141) (or any other means to achieve oscillating reciprocation) to cut any occasional foliage stems which, while in operation, get caught on said leading-edge, thus eliminating any clogging.

Figure 7:
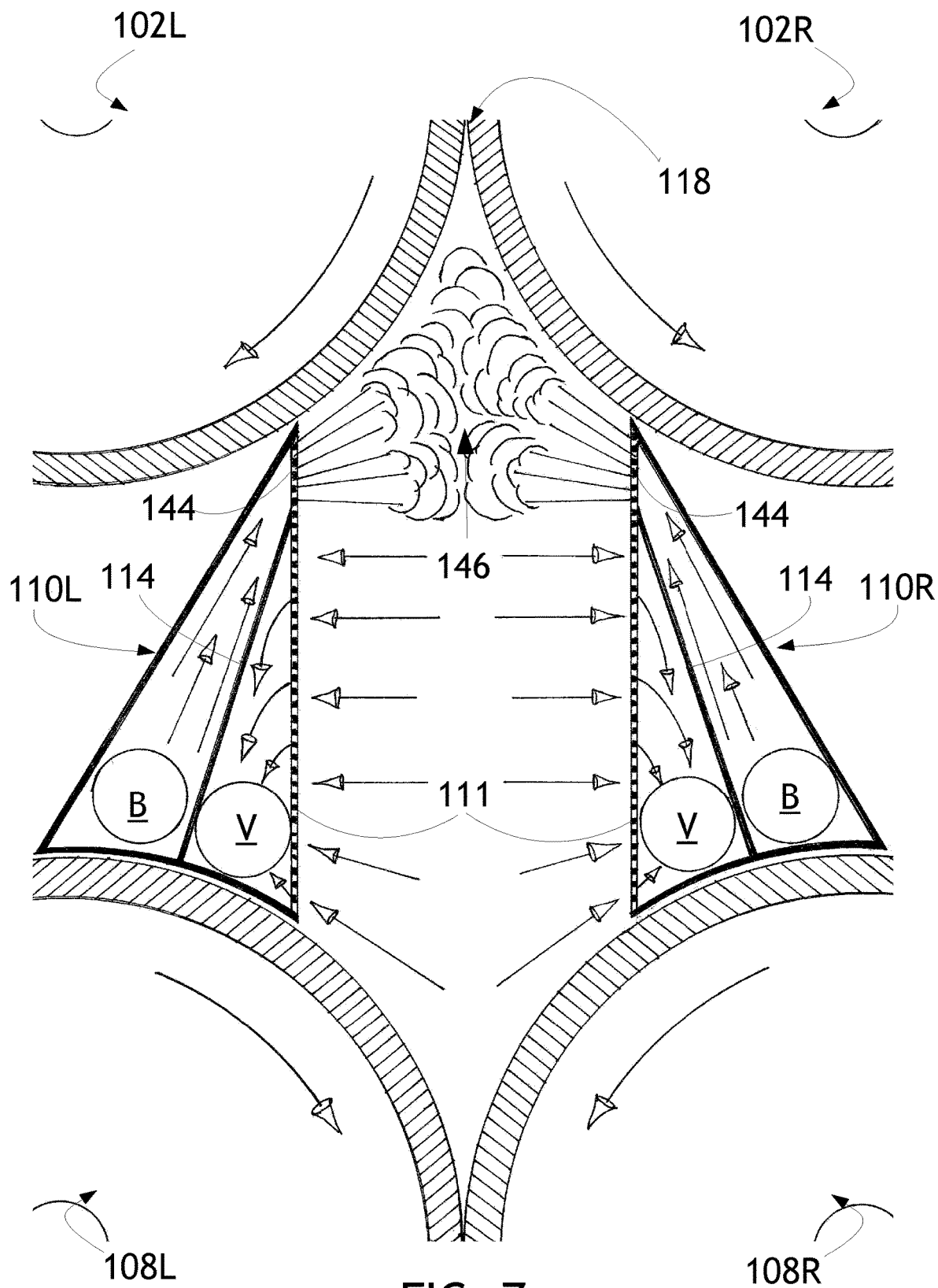
FIG. 7 is a top plan view of a single pollen recirculation chamber used in the pollination machine of FIG. 1, showing the air circulation patterns therein.

In further describing this Pollinating Machine, atop pollinating station #1 (30A), is mounted a high-volume, adjustable-speed, electric air vacuum/blower (130), (which is powered by an electrical generator, on-board the tractor). The "intake" housing of the vacuum/blower is connected to the hole in the top-plate (V) (FIGS. 2 and 7) of both the left three-sided-structure (110L) and the right three-sided-structure (110R), by semi-flexible vacuum duct-pipes (131A). This configuration vacuums pollen-laden air from the "pollen recirculation chamber" (via the perforated face-plates) (111) of pollinating station #1 (30A) through the top-hole (V) of each three-sided-structure (10L & 10R) and blows it through blower duct-pipes (133A) into the top-plate holes (B) of the left air-duct passageway and the right air-duct passageway, of pollinating station #2 (30B). The pollen continues to be blown into the air-duct passageways, and out the 10%-perforated portion (144) of the baffle-plate (114). This creates a "pollen bath" or "pollen screen" (146) proximate entry seam (118), which the "tripping" blossoms immediately emerge into and through, from exiting the front companion rollers (102L & 102R). This "pollen-bath" completely engulfs each tripping blossom in foreign pollen before the tripped blossoms' own pollen can clog their own stimgas. The same afore described configuration also exists between pollinating station #2 (30B), and #3 (30C), that is to say, vacuumed pollen-laden air from pollinating station (30B) through vacuum duct-pipes (131B) blows through blower duct-pipes (133B) into pollinating station #3 (30C), and finally, vacuumed pollen-laden air from station #3 (30C) through vacuum duct-pipes (131C) blows back through blower duct-pipes (133C) into station #1 (30A). A conductive-metal grounding-chain (147), connected to the frame 100, drags on the ground (FIG. 1) to dissipate static electricity created by the blowing pollen, which may hinder the flow of the blowing pollen through the system.

In other words, as the pollinating machine drives through a field of blooming alfalfa plants (preferably in rows, but not necessarily), the funneling-wings (128) and guards (129) lift and direct the foliage into the front companion-rollers (102L & 102R) of station #1 (30A), pressing the blossoms firmly enough to collapse each keel-pedal enclosure. Held in place by the compression of the soft rollers, the pistols cannot yet "trip," but upon emerging out of the front-companion rollers, "spring-loaded" pistols then immediately "trip" by the thousands, each creating a tiny dust-cloud of pollen, all within the enclosed "pollen-recirculating chamber". This pollen is immediately vacuumed out of station #1 (30A) and blown into station #2 (30B), directly into the emerging and "tripping" blossoms coming through station #2's front companion-rollers (102L) & (102R). At the same time, the thousands of tiny "dust clouds" of pollen being generated from the tripping blossoms in station #2 are vacuumed out and blown into station #3, and the pollen dust from station #3 is vacuumed out and recirculated back to station #1. With the entire system being mostly sealed, the recirculating pollen continues to accumulate and condense in the recirculating, forced air. Since the pollen-grains are not sticky, and in general, do not adhere to the leaves, stems, or equipment, but only adhere to the stigmas, which are very sticky, of each tripped-blossom, where they are crucially needed. All the pollen being recirculated through the 3 stations, via the duct-pipes, is 100% foreign to the blossoms it blows onto and, therefore, successfully cross-pollinates them all.

In other words, by the time pollen from one plant in any given row is vacuumed in and recirculated through all 3 stations, back to its original station, the machine has traveled ahead to other plants in that same row. Thus, every blossom is receiving purely foreign pollen (not of its own plant), even though the system eventually recirculates pollen back through itself, repeatedly. And as it is all "foreign" pollen being blown directly into the "tripping" stigmas of each flower, the highly concentrated pollen replicates that which would be carried on the heads of leaf-cutter bees, to each flower. Therefore, the ever-accumulating, highly concentrated flow of blowing pollen, being precisely directed, successfully ensures that foreign pollen-grains are positioned on, or under, every stigma, in the split-second that it "trips." Thus, foreign pollen grains attach to each stigma before its own self-sterile pollen inundates it. Therefore, by cross-pollinating each blossom, alfalfa seed is produced on an enormous scale, uniformly, throughout the entire field, independent of bees.

Various modifications may be made to the pollination machine and still be within the purview of the invention. The pollination machine may be constructed to work with a single pollination chamber so long as the pollen is delayed by about 1 second, the time it takes, on average, for a plant to pass through the machine. In so doing, the donor plant is no longer in the chamber and the recently tripped plant will be bathed in its pollen. Likewise, the machine has been described with specific reference to alfalfa and has been designed with the specific structure of alfalfa in mind. It should be readily appreciated that the generation of seed from other plants, particularly those requiring cross-pollination, may be benefitted by this invention. Further, it should be noted that pollen is, in and of itself, a cash crop and may be harvested by placing collectors in the air stream and, if necessary, preventing the blowing back of pollen into the chamber.

Although the present invention has been described with reference to preferred embodiments, numerous modifications and variations can be made and still the result will come within the scope of the invention. No limitation with respect to the specific embodiments disclosed herein is intended or should be inferred.

INDUSTRIAL APPLICABILITY

The present invention has industrial applicability in that it may be made in industry and has particular use in the agricultural industry.

What is claimed is:
1. A pollination machine comprising at least one pollen recirculation chamber, each of the at least one pollen recirculation chamber being defined by a pair of front rollers, a pair of rear rollers, and at least two perforated sidewalls;
    at least one vacuum vent in fluid communication with at least one perforation of at least one of the at least two perforated sidewalls;
    at least one blower vent in fluid communication with at least one perforation of at least one of the at least two perforated sidewalls and further directed towards the pair of front rollers; and
    a manifold connecting the at least one vacuum vent and at least one blower vent in fluid communication with each other;
    wherein plants enter the at least one pollen recirculation chamber through the pair of front rollers, triggering a release of pollen from the plants, and exit through the pair of rear rollers, while the at least one blower vent inundates the plants with previously collected pollen upon entry and the at least one vacuum vent is used to collect pollen released by the plants for redirection by the at least one blower vent towards a seam between the pair of front rollers.

2. The pollination machine of claim 1, the at least one pollen recirculation chamber being a plurality of pollen recirculation chambers and wherein the at least one vacuum vent of one of the plurality of pollen recirculation chambers is in direct fluid communication with the at least one blower vent of another of the plurality of pollen recirculation chambers such that pollen collected from one pollen recirculation chamber is deposited in another pollen recirculation chamber.

3. The pollination machine of claim 2 comprising three pollen recirculation chambers, wherein the air from a first pollen recirculation chamber is directed into a second pollen recirculation chamber from which air is then directed into a third pollen recirculation chamber and from there back into the first pollen recirculation chamber.

4. The pollination machine of claim 1, further comprising a delay structure wherein airflow, and associated pollen, between the vacuum vents and the blower vents is then delayed until a plant that enters the pollen recirculation chamber can leave the recirculation chamber.

5. The pollination machine of claim 1 each blower vent further comprising a plurality of vent fins which divide airflow flowing through the vents into a plurality of vent chambers which specifically direct the divided airflow into the pollen recirculation chambers.

6. The pollination machine of claim 5, the at least one pollen recirculation chamber being a plurality of pollen recirculation chambers and wherein the at least one vacuum vent of one of the plurality of pollen recirculation chambers is in direct fluid communication with the at least one blower vent of another of the plurality of pollen recirculation chambers such that pollen collected from one pollen recirculation chamber is deposited in another pollen recirculation chamber.

7. The pollination machine of claim 6, comprising three pollen recirculation chambers, wherein the air from a first pollen recirculation chamber is directed into a second pollen recirculation chamber from which air is then directed into a third pollen recirculation chamber and from there back into the first pollen recirculation chamber.

8. The pollination machine of claim 5, further comprising a delay structure wherein airflow, and associated pollen, between the vacuum vents and the blower vents is then delayed until a plant that enters the pollen recirculation chamber can leave the recirculation chamber.

* * * * *